United States Patent [19]
Peurrung

[11] Patent Number: 5,658,233
[45] Date of Patent: Aug. 19, 1997

[54] NEUTRON CAPTURE THERAPY WITH DEEP TISSUE PENETRATION USING CAPILLARY NEUTRON FOCUSING

[75] Inventor: Anthony J. Peurrung, Richland, Wash.

[73] Assignee: Battelle Memorial Institute, Richland, Wash.

[21] Appl. No.: 529,969

[22] Filed: Sep. 19, 1995

[51] Int. Cl.⁶ ........................................ A61N 5/00
[52] U.S. Cl. ................................ 600/1; 250/251
[58] Field of Search ................... 600/1–8; 604/20, 604/21; 250/251

[56] References Cited

U.S. PATENT DOCUMENTS

| | | | |
|---|---|---|---|
| 4,510,924 | 4/1985 | Gray | 600/3 |
| 4,969,863 | 11/1990 | van't Hooft et al. | 600/7 |
| 5,037,374 | 8/1991 | Carol | 600/1 |
| 5,084,002 | 1/1992 | Liprie | 600/7 |
| 5,433,693 | 7/1995 | Ott | 600/1 |
| 5,497,008 | 3/1996 | Kumakhov | 250/505.1 |
| 5,547,754 | 8/1996 | Horn et al. | 600/1 |

FOREIGN PATENT DOCUMENTS 0422899  5/1992  Japan.

*Primary Examiner*—Lee S. Cohen
*Assistant Examiner*—Bryan K. Yarnell
*Attorney, Agent, or Firm*—Douglas E. McKinley, Jr.

[57] ABSTRACT

An improved method for delivering thermal neutrons to a subsurface cancer or tumor which has been first doped with a dopant having a high cross section for neutron capture. The improvement is the use of a guide tube in cooperation with a capillary neutron focusing apparatus, or neutron focusing lens, for directing neutrons to the tumor, and thereby avoiding damage to surrounding tissue.

4 Claims, 1 Drawing Sheet

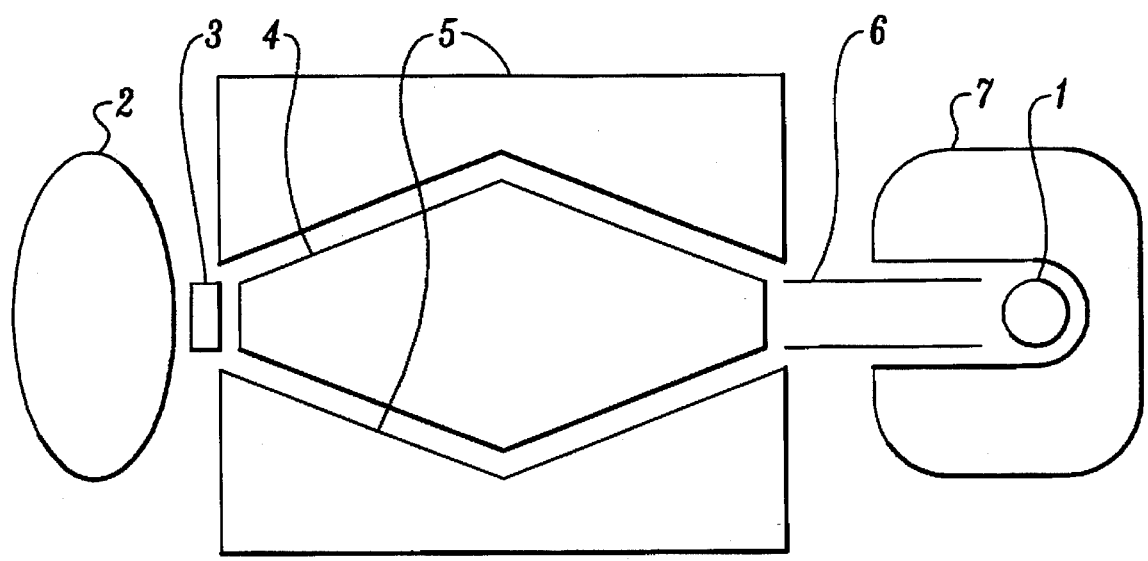

NEUTRON CAPTURE THERAPY WITH DEEP TISSUE PENETRATION USING CAPILLARY NEUTRON FOCUSING

This invention was made with Government support under Contract DE-AC06-76RLO 1830 awarded by the U.S. Department of Energy. The Government has certain rights in the invention.

FIELD OF THE INVENTION

The present invention relates generally to a radiotherapy method for treating a subsurface cancer or tumor. More specifically, the present invention provides an improved method for delivering thermal neutrons to a subsurface cancer or tumor which has been first treated with a reagent having a high cross section for neutron capture. The improvement comprises the use of a guide tube in cooperation with a capillary neutron focusing apparatus, or neutron focusing lens, for directing neutrons to the tumor, and thereby avoiding damage to surrounding tissue.

BACKGROUND OF THE INVENTION

The use of Neutron Capture Therapy (NCT) for treatment of cancer or tumors is well known by those skilled in the art. NCT operates as a several step process. First, a reagent having a high cross section for neutron capture is selected. Presently, the use of gadolinium and boron as reagents is preferred by those skilled in the art. The reagent must then be combined with a pharmaceutical compound which is selectively absorbed by tumor cells. The combined pharmaceutical compound and reagent are administered to the patient, whereupon the reagent is selectively absorbed by tumor cells. Several compounds containing suitable reagents which are selectively absorbed by tumor cells are known in the art, including, but not limited to, borane sodium borocaptate, boronophenylalanine, boronated monoclonal antibodies, and gadolinium contrast agents. Next, neutrons are directed towards the tumor site. By virtue of the large cross section for neutron capture exhibited by the reagent as compared with the cross section of other elements found in surrounding tissue, the reagent will preferentially capture neutrons to the exclusion of the surrounding tissue. Upon exposure to neutrons, tissue containing reagent absorbs or captures neutrons and the reagent decays. Upon neutron capture, decay of the reagent releases high intensity, non-penetrating energy which destroys the cell immediately surrounding the reagent. Since the reagent is preferentially absorbed by tumor cells, the tumor cells are thereby likewise preferentially destroyed during the decay of the reagent to the exclusion of damage to the surrounding healthy tissue.

The use of NCT as an effective therapy for treating tumors has suffered from drawbacks associated with the introduction of neutrons to the tumor site. Most problematic is the introduction of neutrons to tumors buried beneath or covered by healthy and critical tissue. For example, those skilled in the art have recognized a need for a method for introducing neutrons to tumors located deep in critical tissue inside a patient, such as the patient's brain, without damage to the surrounding tissue. This need may be attributed to the characteristics of the neutrons themselves, and the effects of neutron bombardment on healthy tissue.

Neutrons may be classified according to the energy they exhibit. High energy neutrons, or fast neutrons, are typically recognized as neutrons emanating from unmoderated sources and having energies greater than about 0.5 MeV. Fast neutrons may be readily generated by methods well known in the art, and then administered to a patient. Fast neutrons penetrate tissue well, thus they can easily penetrate to reach tumors deeply imbedded in otherwise healthy tissue. However, fast neutrons suffer from a variety of drawbacks preventing their effective use in NCT. Fast neutrons cannot be aimed effectively using neutron focusing lenses, as the energy in fast neutrons is sufficient to cause the neutrons to escape the refraction of the interior walls of the lenses. Thus, when administered to a patient, fast neutrons cannot be directed exclusively to the tumor site. Also, fast neutrons scatter upon collisions with hydrogenated molecules typical of tissue and deposit excessive energy during those collisions within healthy cells surrounding the tumor site, which may damage the cells. The effects of (a) the inability to focus fast neutrons with neutron focusing lenses and (b) the scattering of the neutrons, insures that exposure of tissue to fast neutrons is not limited to the tumor site, and that healthy tissue surrounding the tumor site will therefore be damaged.

Intermediate energy neutrons, or epithermal neutrons, are partially moderated and are typically recognized as neutrons with energy ranging from about 0.2 eV to about 10 keV. Epithermal neutrons also exhibit sufficient energy to penetrate tissue to depths sufficient to reach deep tumors. Because of their lower energy, epithermal neutrons are in many ways superior to fast neutrons when used in NCT. Specifically, epithermal neutrons are of low enough energy that during collisions with healthy cells, insufficient energy is deposited in the healthy cells to cause damage. However, procedures and techniques known in the art for generating epithermal neutrons are expensive, and it is difficult to attain a consistent energy level among the generated epithermal neutrons. Also, epithermal neutrons exhibit the scattering observed in fast neutrons, which causes irradiation of healthy tissue surrounding the tumor.

Thermal and cold neutrons exhibit energy below that of epithermal neutrons. Fast neutrons are readily converted, or moderated, to thermal neutrons by directing them through hydrogenous materials at about room temperature. Thermal neutrons are generally recognized as completely moderated neutrons having an average energy of about 0.025 eV. By cooling the hydrogenous moderator below room temperature, cold neutrons having energy below about 0.025 eV are produced. The collisions of the fast neutrons with hydrogen nuclei dissipates the kinetic energy, thus thermalizing the neutrons. In general, a reduction in energy in the neutrons improves the ability of a reagent to capture the neutrons. Thus, both thermal and cold neutrons (hereafter both thermal and cold neutrons being jointly referred to as cold so that the term "cold" as used hereinafter refers to neutrons having energies less than about 0.025 eV) are rapidly captured by suitable reagents having high cross sections for neutron capture. However, the loss of energy renders cold neutrons unable to penetrate tissue to a depth sufficient to allow capture by reagents absorbed in tumors deep with tissue.

Previously, limitations in the ability to control the trajectory of cold neutrons limited the effective use of cold neutrons in treating tumor sites because cold neutrons could not be directed exclusively at a tumor site and surrounding tissue would invariably be exposed to neutron attack. NCT thus resulted in the irradiation of not only tumors, but the surrounding tissue with cold neutrons. However, recent advances in capillary neutron optics have allowed great increases in the precision with which neutrons may be delivered to a given location, such as a tumor. Neutron focusing lenses, consisting of bundles of hollow capillaries, have been developed which allow thermal neutrons to be focused. By focusing cold neutrons towards a tumor site treated with a reagent having a high cross section for neutron capture, the tumor may be treated with minimal neutron attack on the surrounding tissue. Still, the advances in NCT enabled by neutron focusing lenses have not completely resolved the limitations of using cold neutrons in NCT for deep tumors because cold neutrons still lack sufficient penetration to reach deep tumors. Thus, those skilled in the art recognize a need for a method for providing cold neutrons to a deep tumor site without damaging the surrounding tissue.

SUMMARY OF THE INVENTION

The invention is an improved method for directing cold neutrons to a deep tumor. A source of cold neutrons is first provided by directing neutrons through a moderator. Then, the cold neutrons are directed through a neutron focusing lens. The improvement comprises the use of a guide tube inserted into a patient's healthy tissue surrounding the tumor. By inserting the guide tube through the surrounding healthy tissue, a pathway is provided for the cold neutrons from the neutron focusing lens to the tumor site.

OBJECTS

It is an object of the invention that a guide tube provide a pathway for cold neutrons to travel to a tumor site located beneath a cross section of tissue, wherein the cross section of tissue is of a sufficient thickness that the tissue would normally prevent the penetration of cold neutrons to the tumor site.

It is a further object of the invention that the cold neutrons are preferentially directed to the tumor site with minimal interaction of the neutrons and the tissue surrounding the tumor.

It is yet a further object of the invention that the cold neutrons delivered to the tumor site are at an energy level wherein the neutrons exhibit minimal scattering and may be selectively adsorbed by reagents within the tumor having a high cross section for neutron capture.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWING

The FIGURE is a schematic drawing of the present invention.

DESCRIPTION OF THE PREFERRED EMBODIMENT

In the preferred embodiment of the instant invention (FIGURE), an improved method for directing cold neutrons to a tumor 1 treated with a neutron capture reagent is provided. A source 2 of cold neutrons having energy less than about 0.025 eV, and preferably having energy less than about 0.002 eV, is first provided by moderating fast neutrons produced by a fast neutron source 2 with a hydrogenous, moderating material 3. Any hydrogenous material will suffice; preferred materials include, but are not limited to, water, paraffin and polyethylene. The temperature of the moderating material 3 will determine the energy of the neutrons leaving the moderating material 3. It is preferred that the energy of neutrons be minimized; thus, while the moderating material 3 may be at or below room temperature, it is preferred that the moderating material 3 be cooled to a temperature between about absolute zero and 20° K. After passing through the moderating material 3, the now cold neutrons are then focused with a neutron focusing lens 4. Neutron focusing lenses 4 known in the art consist of a plurality of capillaries having an index of refraction to neutron propagation sufficient to internally reflect cold neutrons in the interior of the capillaries, thereby allowing the neutrons to be directed towards a target and focused at a given focal length. X-Ray Optical Systems, Inc. of Albany, N.Y., currently manufactures neutron focusing lenses 4 useful in the instant invention. In a preferred embodiment, a shielding material 5 is positioned surrounding the moderating material 3 to prevent the passage of fast neutrons from the fast neutron source 2 from reaching the patient. Any material known in the art for shielding fast neutrons, including but not limited to lead and bismuth, is appropriate for use as a shield 5. The use of a shield 5 insures that only neutrons which have passed through the moderating material 3 and have thus been cooled or thermalized will reach the patient.

The improvement comprises use of a guide tube 6 allowing passage of focused neutrons from the neutron focusing lens 4 to the tumor 1. By positioning a guide tube 6 such that a passage way through healthy tissue 7 is provided for the cold neutrons focused by the neutron focusing lens 4, a high concentration of non-penetrating cold neutrons may be effectively administered to a tumor 1 deeply embedded in healthy tissue 7 without exposing the surrounding healthy tissue 7 to neutrons. The guide tube 6 may be of any proportion or shape as required by the particular application. For example, a cylindrical guide tube 6 would typically be appropriate with the length and circumference of the guide tube 6 being dictated by the depth of the tumor in the patient and properties including, but not limited to, the focal length, the radius, the focal radius, and the transmission efficiency of the neutron focusing lens 4. For example, a cylindrical guide tube 6 may have an inside diameter from about 2 mm to about 4 cm and a length up to 20 cm, and may be constructed of any material suitable for insertion into a patient including, but not limited to, glass, metal, or plastic. All that is required is that the guide tube 6 provide a passage way free of neutron scattering or absorbing material in between the neutron focusing lens 4 and the tumor 1.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An improved method for directing cold neutrons to a tumor treated with a neutron capture reagent wherein a source of cold neutrons is first provided, said cold neutrons are then focused with a neutron focusing lens wherein the improvement comprises:

providing a guide tube through healthy tissue for guiding focused neutrons from the neutron focusing lens to the tumor.

2. The method of claim 1, wherein said cold neutrons are provided at an energy below about 0.025 eV.

3. The method of claim 1, wherein the guide tube has an internal diameter between about 2 mm and about 4 cm.

4. The method of claim 1, wherein the guide tube has a length of less than 20 cm.

\* \* \* \* \*